(12) United States Patent
Liang

(10) Patent No.: US 7,460,288 B2
(45) Date of Patent: Dec. 2, 2008

(54) METHODS FOR DETERMINING REFRACTIVE CORRECTIONS FROM WAVEFRONT MEASUREMENTS

(75) Inventor: Junzhong Liang, Fremont, CA (US)

(73) Assignee: AMO Manufacturing USA, LLC, Santa Clara, CA (US)

( * ) Notice: Subject to any disclaimer, the term of this patent is extended or adjusted under 35 U.S.C. 154(b) by 770 days.

(21) Appl. No.: 10/726,733

(22) Filed: Dec. 2, 2003

(65) Prior Publication Data
US 2004/0145702 A1    Jul. 29, 2004

Related U.S. Application Data

(60) Provisional application No. 60/431,622, filed on Dec. 6, 2002.

(51) Int. Cl.
*A61B 3/10* (2006.01)
*A61B 3/14* (2006.01)

(52) U.S. Cl. .................. 359/205; 359/206; 359/209

(58) Field of Classification Search .......... 351/205, 351/206, 209, 211, 221, 243, 210; 359/205, 359/206, 209, 211, 221, 243, 210
See application file for complete search history.

(56) References Cited

U.S. PATENT DOCUMENTS

| | | | |
|---|---|---|---|
| 5,599,340 A * | 2/1997 | Simon et al. ............. 606/4 |
| 5,682,223 A | 10/1997 | Menezes et al. | |
| 5,684,560 A | 11/1997 | Roffman et al. | |
| 5,724,258 A | 3/1998 | Roffman | |
| 5,807,377 A | 9/1998 | Madhani et al. | |
| 6,200,342 B1 | 3/2001 | Tassignon | |
| 6,280,435 B1 | 8/2001 | Odrich et al. | |
| 6,419,671 B1 | 7/2002 | Lemberg | |
| 6,554,429 B1 | 4/2003 | Campin et al. | |
| 6,607,274 B2 | 8/2003 | Stantz et al. | |
| 6,679,606 B2 | 1/2004 | Campin et al. | |
| 6,682,196 B2 | 1/2004 | Sheets, Jr. et al. | |
| 2002/0030824 A1 * | 3/2002 | Wirth ............. 356/512 |
| 2002/0135736 A1 | 9/2002 | Stark et al. | |
| 2002/0140902 A1 | 10/2002 | Guirao et al. | |
| 2002/0167643 A1 | 11/2002 | Youssefi | |

(Continued)

FOREIGN PATENT DOCUMENTS

WO    WO 2004/053568 A1    6/2004

OTHER PUBLICATIONS

Artal, Pablo. "Calculation of two-dimensional foveal retinal images in real eyes" *J. Opt. Soc. Am. A*, vol. 7, No. 8 (Aug. 1990), pp. 1374-1381.

(Continued)

*Primary Examiner*—Scott J. Sugarman
*Assistant Examiner*—Brandi N Thomas
(74) *Attorney, Agent, or Firm*—Townsend and Townsend and Crew LLP

(57) ABSTRACT

A method for determining a refractive correction for an eye involves measuring an optical error of the eye, calculating at least one image quality parameter for a selected spatial frequency of range of spatial frequencies, based on the measured optical error of the eye, and forming a plan for refractive correction of the optical error, based on the calculated image quality parometer. In some embodiments, measuring the optical error involves taking one or more wavefront measurements. In some embodiments, calculating the parameter involves calculation a modulation transfer function.

31 Claims, 11 Drawing Sheets

U.S. PATENT DOCUMENTS

| | | |
|---|---|---|
| 2003/0199858 A1 | 10/2003 | Schelonka |
| 2004/0145702 A1 | 7/2004 | Liang |
| 2004/0169820 A1 | 9/2004 | Dai et al. |
| 2004/0246440 A1 | 12/2004 | Andino et al. |
| 2004/0257530 A1 | 12/2004 | Chernyak et al. |
| 2005/0254006 A1 | 11/2005 | Dai et al. |
| 2005/0270491 A1* | 12/2005 | Dai et al. .................... 351/246 |

OTHER PUBLICATIONS

Greivenkamp, John E. et al. "Visual Acuity Modeling Using Optical Raytracing of Schematic Eyes" *American Journal of Ophthalmology*, vol. 120, No. 2 (Aug. 1995), pp. 227-240.

Liang, Junzhong et al. "Aberrations and retinal image quality of the normal human eye" *J. Opt. Soc. Am. A,* vol. 14, No. 11 (Nov. 1997), pp. 2873-2883.

Liang, Junzhong et al. "Objective Measurement of Wave Aberrations of the Human Eye with the use of a Harman-Shack Wave-front Sensor" *Journal Optical Society of America,* vol. 11, No. 7 (Jul. 1994), pp. 1-9.

Loewenfeld, Irene, E., *The Pupil: Anatomy, Physiology and Clinical Applications,* vol. 1, (© 1993) Wayne State University Press, Detroit, MI, pp. 296, 301-304.

Moreira et al., "Multifocal Corneal Topographic Changes with Excimer Laser Photorefractive Keratectomy" *Arch. Ophthalmol.* (1992) 110:994-999.

Vinciguerra et al., "Excimer Laser Photorefractive Keratectomy for Presbyopia: 24-month Follow-up in Three Eyes" *Journal of Refractive Surgery* (198) 14:31-31.

U.S. Appl. No. 60/431,622 (filed Dec. 6, 2002) in the name of Liang, and entitled "Methods for Determining Refractive Corrections from Wavefront Measurements".

U.S. Appl. No. 60/579,124 (filed Jun. 10, 2004) in the name of the Dai et al., and entitled "Presbyopia Correction Using Patient Data".

U.S. Appl. No. 60/519,885 (filed Nov. 13, 2003) in the name of Dai et al., and entitled "Presbyopia Correction Using Effective Power".

U.S. Appl. No. 60/458,387 (filed May 5, 2003) in the name of Dai et al., and entitled Method for Optimize Laser Vision Correction of Presbyopia.

U.S. Appl. No. 60/468,303 (filed May 5, 2003) in the name of Dai et al., and entitled "Shape Optimization for Presbyopia Correction".

U.S. Appl. No. 60/431,643 (filed Dec. 5, 2002) in the name of Dai et al., and entitled "System and Method for Software Download to Wireless Communication Device".

* cited by examiner

| | Pupil size | spherical aberreration | focus | focus shift | net focus |
|---|---|---|---|---|---|
| 0.25 Z12 | 6.00 | 3.35 ρ⁴ up to 6mm pupil | -0.74 | 0.46 | -0.28 |
| 0.049 Z12 | 4.00 | 3.35 ρ⁴ up to 4mm pupil | -0.34 | 0.05 | -0.29 |

FIG. 10

| c12 (6mm) | 6 mm fit | 4 mm fit | highest MTF at 60 c/d for a 6 mm pupil | highest MTF at 60 c/d for a 4 mm pupil | difference |
|---|---|---|---|---|---|
| -0.7 | 2.09 | 0.92 | 0.59 | 0.52 | 0.07 |
| -0.5 | 1.49 | 0.66 | 0.49 | 0.41 | 0.08 |
| -0.25 | 0.745 | 0.335 | 0.285 | 0.285 | 0 |
| 0 | 0 | 0 | 0 | 0 | 0 |
| 0.25 | -0.745 | -0.335 | -0.285 | -0.285 | 0 |
| 0.5 | -1.49 | -0.66 | -0.49 | -0.41 | -0.08 |
| 0.75 | -2.09 | -0.92 | -0.59 | -0.42 | -0.17 |

FIG. 11

METHODS FOR DETERMINING REFRACTIVE CORRECTIONS FROM WAVEFRONT MEASUREMENTS

CROSS REFERENCE TO RELATED APPLICATIONS

This application claims the benefit of U.S. Provisional Patent Application No. 60/431,622, filed Dec. 6, 2002, entitled "Methods For Determining Refractive Corrections From Wavefront Measurements," which is hereby fully incorporated by reference.

BACKGROUND OF THE INVENTION

The present invention generally relates to vision correction systems. More particularly, the invention relates to improved methods and systems for determining refractive corrections from wavefront measurements.

Laser eye surgical systems typically employ a system that can track and measure optical characteristics of a patient's eye. One promising eye measurement system uses wavefront technology that allows a surgeon to measure and treat low order and high order aberrations in and on the patient's eye. Wavefront measurement of the eye creates a high order aberration map that permits assessment of aberrations throughout the optical pathway of the eye, e.g., both internal aberrations and aberrations on the corneal surface. The aberration information can then be used to compute a custom ablation pattern for allowing a surgical laser system to correct the complex aberrations in and on the patient's eye. Although such wavefront measurements are often described below in the context of laser surgical systems, such measurements may also be used to formulate refractive correction patterns in alternative eye treatment procedures and systems such as for use in radial keratotomy, intraocular lenses, corneal ring implants, and the like.

One exemplary wavefront technology system is the VISX WaveScan™ System, which uses Hartmann-Shack wavefront sensors that can quantify aberrations throughout the entire optical system of the patient's eye, including first- and second-order sphero-cylindrical errors, coma, and third and fourth-order aberrations related to coma, astigmatism, and spherical aberrations. The aberrations in and on the patient's eye can be displayed to the surgeon in the form of an aberration map.

Wavefront aberrations measured with a wavefront sensor provide a map of optical aberration across the pupil of eye. This aberration map can then be used to plan a refractive correction for improving vision quality via wavefront-guided laser vision correction or other vision correction means. Refractive corrections are often determined by Zernike decomposition of wavefront measurements, as proposed by Liang et al., in *Objective Measurement of Wave Aberrations of the Human Eye with the Use of a Harman-Shack Wavefront Sensor*, Journal Optical Society of America, July 1994, vol. 11, No. 7, pp. 1-9, the entire contents of which is hereby incorporated by reference.

Typically, one or more parameters of image quality are used to formulate a refractive correction plan from wavefront measurements. Some of the possible image quality parameters include the Strehl Ratio, root mean squared (RMS), the value of individual Zernike terms, fill-width half-height (FWHH) of the point spread function (PSF), and modulation transfer function (MTF). For example, based on a minimized wavefront root mean square (RMS), spherical and cylindrical corrections can be determined by the second-order Zernike terms. This approach is effective when an eye has few high-order aberrations. When an eye has a significant quantity of high-order aberrations, however, minimizing the wavefront RMS does not necessarily lead to best image quality. Additionally, when the eye has a significant amount of spherical aberration, the refractive correction determined by the second-order Zernike terms will vary significantly depending on the pupil size of wavefront data. For an eye with Zernike spherical aberration equal to 0.35 um for a 6 mm pupil, the difference in spherical correction determined by Zernike decomposition can be as large as 0.93 D for pupil diameters varying from 2 mm to 6 mm. This large variation in refractive corrections, depending on the pupil size, contradicts the results seen in clinical refraction and can make the use of wavefront measurements for determining refractive corrections difficult.

Another commonly used parameter is the Strehl Ratio, with a maximized Strehl Ratio often being used to determine refractive correction. The Strehl Ratio, however, covers the total MTF volume up to a cutoff spatial frequency that is typically around 180 cycles/degree for a 6 mm pupil. Spatial frequencies higher than about 60 cycles/degree have little or no bearing on actual vision, because the Nyquist frequency limit dictates that the average retinal receptor is capable of only about 57 cycles/degree. Thus, the Strehl Ratio may include information which is not helpful for refractive correction determination.

Therefore, it would be advantageous to have improved methods and systems for using wavefront measurements of an eye to determine refractive corrections for the eye. Such methods and systems would ideally provide refractive correction patterns which would correlate to vision quality measured in vision tests. Additionally, refractive correction should ideally apply across a variety of pupil sizes. At least some of these objectives will be met by the present invention.

BRIEF SUMMARY OF THE INVENTION

The present invention generally provides improved methods and devices for determining refractive corrections from measurements of optical error, such as wavefront measurements. The invention is particularly useful for enhancing the accuracy and efficacy of laser eye surgical procedures such as photorefractive keratectomy (PRK), phototherapeutic keratectomy (PTK), laser in situ keratomileusis (LASIK), and the like, and can be easily adapted for use with existing laser systems. Although methods and systems of the invention are described in the context of laser eye surgery, however, it should be understood the methods and systems may be adapted for use in alternative eye treatment procedures and systems such as for use in radial keratotomy, intraocular lenses, corneal ring implants, and the like.

In one aspect of the invention, a method for determining a refractive correction for an eye includes: measuring an optical error of the eye; calculating at least one image quality parameter for a selected spatial frequency or range of spatial frequencies, based on the measured optical error of the eye; and forming a plan for refractive correction of the optical error, based on the calculated image quality parameter. In some embodiments, measuring the optical error comprises measuring at least one wavefront aberration with a wavefront of light passing through the optical components of the eye, using a wavefront sensor. Optionally, the wavefront aberration is measured with the pupil of the eye having a diameter of between about 4 mm and about 6 mm.

The step of calculating at least one image quality parameter may comprise, for example, calculating at least one modulation transfer function. This may involve, in some embodiments, calculating a plurality of modulation transfer functions corresponding to a plurality of potential refractive corrections. In such embodiments, forming a plan for refractive correction may comprise selecting one of the potential refractive corrections, wherein the selected refractive correction corresponds to a highest modulation transfer function of the plurality of modulation functions, at the selected spatial frequency. In other embodiments, forming a plan for refractive correction comprises selecting one of the potential refractive corrections, wherein the selected refractive correction corresponds to a largest total volume modulation transfer function of the plurality of modulation functions, over the selected range of spatial frequencies. In still other embodiments, forming a plan for refractive correction comprises selecting one of the potential refractive corrections, wherein the selected refractive correction corresponds to a highest average modulation transfer function of the plurality of modulation functions, over the selected range of spatial frequencies.

Sometimes, alternatively, calculating at least one image quality parameter comprises calculating at least one modified Strehl ratio. For example, calculating at least one modified Strehl ratio may involve calculating a plurality of modified Strehl ratios corresponding to a plurality of potential refractive corrections within the selected range of spatial frequencies comprising about 0 cycles/degree to about 60 cycles/degree. Optionally, in some of these embodiments, forming a plan for refractive correction comprises selecting one of the potential refractive corrections, wherein the selected refractive correction corresponds to a highest modified Strehl ratio of the plurality of modified Strehl ratios.

Generally, any suitable spatial frequency or range of frequencies may be used. For example, in one embodiment the selected spatial frequency comprises about 30 cycles/degree. In other embodiments, the selected spatial frequency may comprise about 37.5 cycles/degree, about 48 cycles/degree, about 60 cycles/degree or any other suitable frequency. In one embodiment, the range of spatial frequencies comprises about 0 cycles/degree to about 60 cycles/degree. Other ranges may comprises about 20 cycles/degree to about 60 cycles/degree, about 0 cycles/degree to about 80 cycles/degree, or the like.

In some embodiments, forming a plan for refractive correction comprises calculating an ablation pattern for a corneal tissue of the eye, based at least partly on the calculated image quality parameter. The method may further comprise ablating the corneal tissue of the eye according to the ablation pattern.

In another aspect, a system for determining a refractive correction for an eye comprises a sensor for measuring an optical error of the eye and a processor for generating a refractive correction pattern based at least in part on an image quality parameter for a selected spatial frequency or range of spatial frequencies, the image quality parameter being based on the optical error. In some embodiments, the sensor comprises a wavefront sensor. In some embodiments, the image quality parameter comprises at least one modulation transfer function. Alternatively, the image quality parameter may comprise at least one modified Strehl ratio. For example, the modified Strehl ratio may comprise a Strehl ratio limited to a range of spatial frequencies of between about 0 cycles/degree and about 60 cycles/degree. In some embodiments, the refractive correction pattern comprises an ablation pattern of laser energy for ablation of a corneal tissue of the eye so as to correct the measured optical error. In such embodiments, the system may further comprise a laser system for directing laser energy onto the corneal tissue of the eye to achieve the generated ablation pattern.

In another aspect, a system for correcting an optical error of an eye comprises a sensor for measuring the optical error of the eye, a processor for generating an ablation pattern of laser energy for ablation of a corneal tissue of the eye so as to correct the measured optical error, the ablation pattern based at least in part on an image quality parameter for a selected spatial frequency or range of spatial frequencies, the image quality parameter being based on the optical error, and a laser system for directing laser energy onto the corneal tissue of the eye to achieve the generated ablation pattern.

In still another aspect, a device for determining a refractive correction for an eye, the device comprising a software module for processing at least one measurement of the eye to provide the refractive correction of the eye. In some embodiments, the measurement comprises at least one wavefront measurement. In some embodiments, the software module calculates at least one modulation transfer function, based on the at least one measurement.

BRIEF DESCRIPTION OF THE DRAWINGS

FIG. 10 is a chart showing focus for optimizing visual acuity with both a 4 mm pupil and a 6 mm pupil, according to one embodiment of the invention.

FIG. 11 is a chart showing consistent results of refractive corrections for both 4 mm pupils and 6 mm pupils with different amounts of spherical aberration, according to one embodiment of the invention.

DETAILED DESCRIPTION OF THE INVENTION

The present invention generally provides improved methods and devices for determining refractive corrections from measurements of optical error, such as wavefront measurements. The invention is particularly useful for enhancing the accuracy and efficacy of laser eye surgical procedures such as photorefractive keratectomy (PRK), phototherapeutic keratectomy (PTK), laser in situ keratomileusis (LASIK), and the like, and can be easily adapted for use with existing laser systems. Although methods and systems of the invention are described in the context of laser eye surgery, however, it should be understood the methods and systems may be adapted for use in alternative eye treatment procedures and systems such as for use in radial keratotomy, intraocular lenses, corneal ring implants, and the like. All references referred to in this application are hereby incorporated herein by reference.

Figure 1:
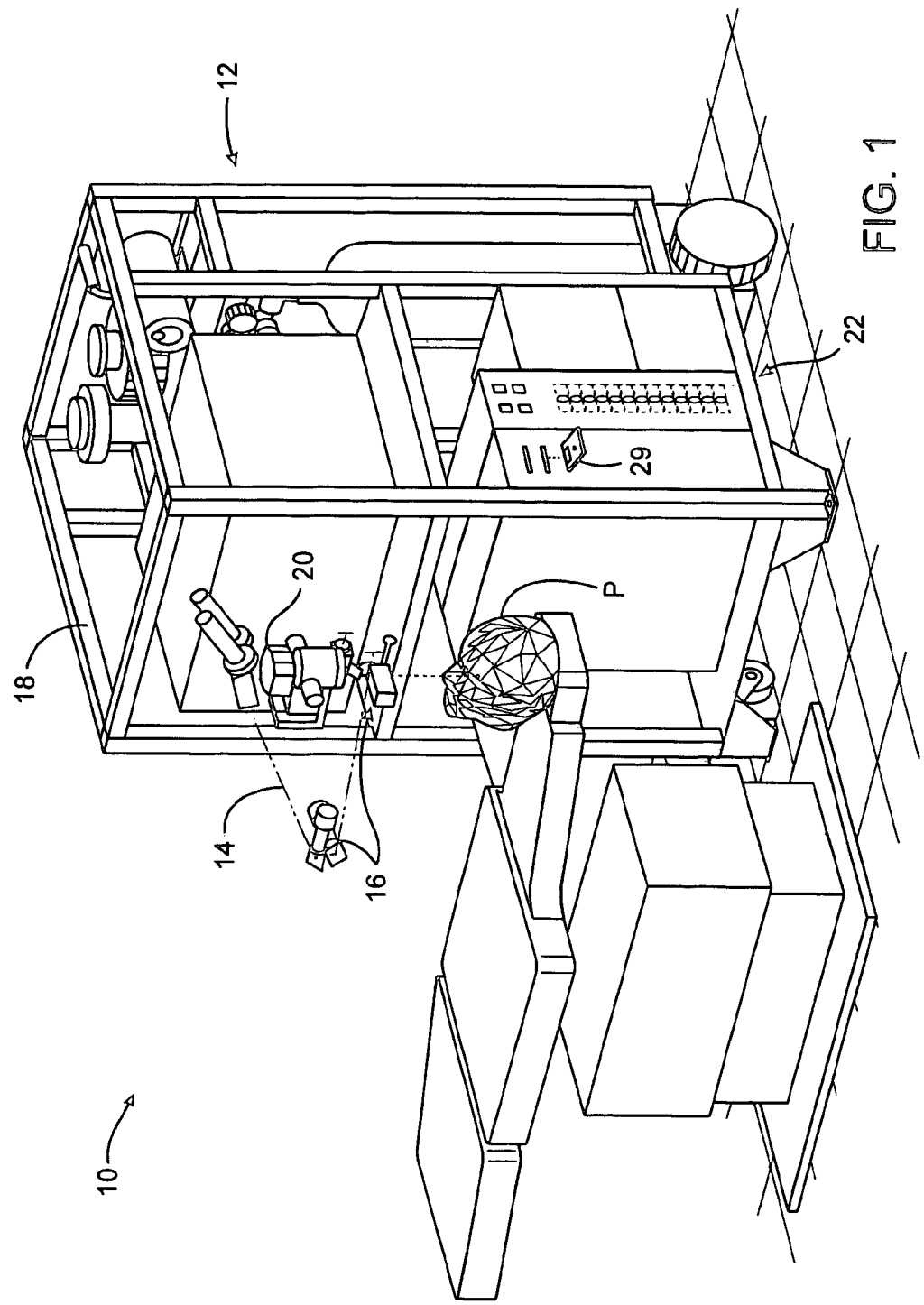
FIG. 1 is a perspective view of a laser eye surgery system.

Referring now to FIG. 1, a laser eye surgery system 10 which may make use of methods and/or devices of the present invention suitably includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of eye E. A similar laser eye surgery system 10 is described in U.S. patent application Ser. No. 09/960,163, Publication No. US 2002/0097375, the entire disclosure of which is hereby incorporated by reference.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 205 nm and/or those which utilize frequency-multiplying techniques. Hence, although an excimer laser is the illustrative source of an ablating beam, other lasers may be used in the present invention.

Laser 12 and delivery optics 16 will generally direct laser beam 14 to the eye of patient P under the direction of a computer 22. Computer 22 will generally selectively adjust laser beam 14 to expose portions of the cornea to the pulses of laser energy so as to effect a predetermined sculpting of the cornea and alter the refractive characteristics of the eye. In many embodiments, both laser 14 and the laser delivery optical system 16 will be under computer control of processor 22 to effect the desired laser sculpting process, with the processor ideally altering the ablation procedure in response to inputs from the optical feedback system described hereinbelow. The feedback will preferably be input into processor 22 from an automated image analysis system, or may be manually input into the processor by a system operator using an input device in response to a visual inspection of analysis images provided by the optical feedback system. Processor 22 will often continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913 (the full disclosure of which is incorporated herein by reference) and as demonstrated by other scanning laser systems such as the LaserScan LSX® laser by LaserSight® Technologies, Inc., LADARVision® by Alcon/Autonomous, and the 217C by Technolas® 217A excimer laser by Bausch & Lomb; using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

As mentioned above, laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying steps or programming instructions for any of the methods of the present invention. Tangible storage media 29 may take the form of a floppy disk, an optical disk, a data tape, a non-volatile memory, or the like, and the processor 22 will include the memory boards and other standard components of modern computer systems for storing and executing this code.

Figure 2:
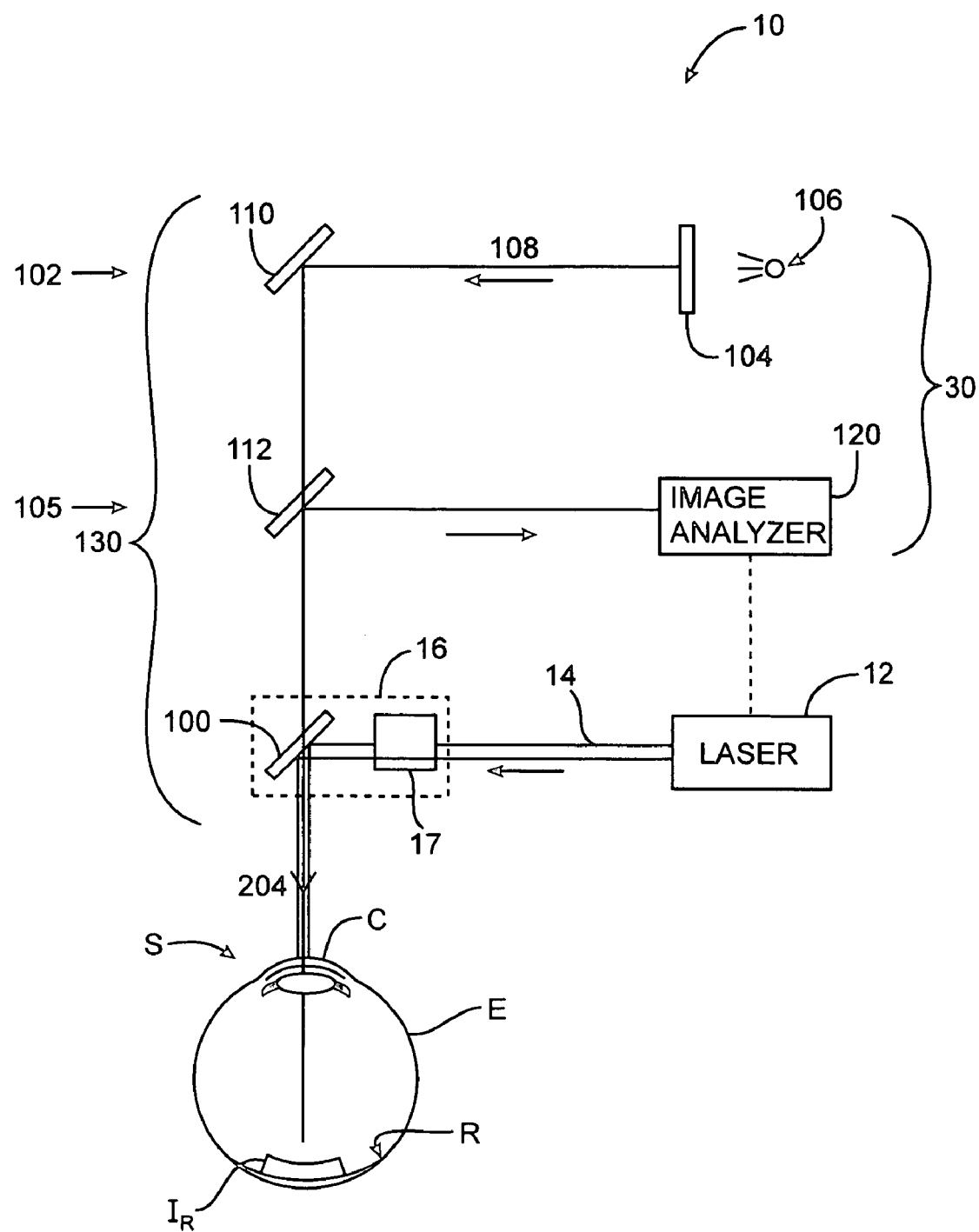
FIG. 2 is a simplified schematic of a laser eye surgery system.

Referring now to FIG. 2, a simplified schematic of the laser eye surgery system 10 shows the optical components used in an optical feedback system 30. Laser 12 directs the laser beam 14 at a beam splitter 100 of the laser delivery optical system 16, often via ablation patterning means 17. As described above, ablation patterning means 17 may include scanning mechanisms (such as offset lenses, mirrors, prisms, or the like), variable profiling mechanisms (such as variable diameter iris diaphragms, variable width slits, zoom lens systems, selectable masks, or the like) and/or energy tailoring mechanisms (such as ablatable masks or gels, diffractive optics, or the like). Beam splitter 100 redirects beam 14 and its pattern of ablation energy towards the eye E to reshape cornea C. This resculpting of cornea C will often be performed after removing or displacing an epithelial layer of the cornea and/or a flap including epithelial tissue, Bowman's Membrane, and stromal tissue (as is well described in the patent literature), or may possibly be focused through the epithelial layer and Bowman's Membrane with an intrastromal system. To provide feedback regarding the effects of the laser ablation procedure on the eye, system 10 generally includes projection optics 102 and imaging optics 105 arranged to project onto and image from a surface of a retina R of eye E. As seen in FIG. 2, at least some of the optical components of projection system 102, imaging system 105, and laser delivery system 106 may be used by more than one of the systems.

In addition to cornea C, eye E includes a number of other components which will affect the eye's overall optical performance, including the lens, iris, anterior and posterior chambers, etc. These and the other optical components of the eye, including cornea C, are generally referred to herein as the ocular optical system S. To provide feedback on the actual results of the resculpting of cornea C, and advantageously, on the changes in optical properties of the overall ocular optical system S, optical feedback system 30 both projects and images an image IR on retina R of eye E.

Figure 3A:
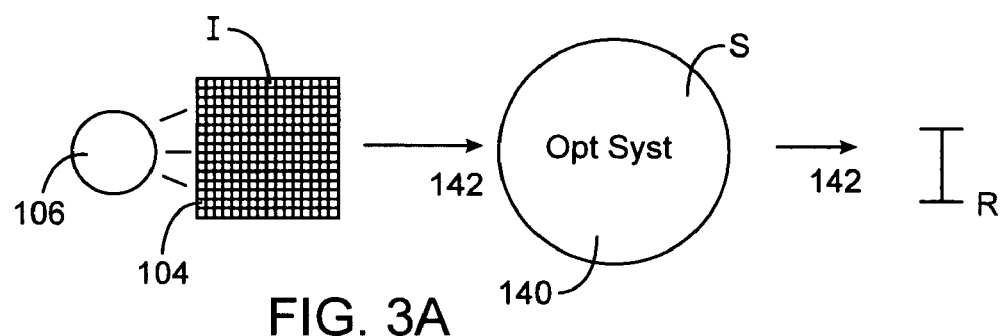
FIGS. 3A and 3B are functional block diagrams schematically showing systems and methods for measuring quality of a corneal optical system by projection and imaging an image through the corneal optical system.

As can be understood with reference to FIGS. 2 and 3A, a target object 104 (which defines a reference image I) is used to project image I on the retina of the eye E to form retinal image IR. The object 104 may be self-illuminating or have an energy source 106 such as a light emitting diode, a laser diode, or a light bulb to direct light rays 108 carrying the reference image I from object 104 towards the eye E. A beam splitter 110 may be used to direct the energy rays towards the eye E. The reference image IR may also be projected using energy outside of the visible spectrum, such as (but not limited to) infrared energy. The imaging quality of retinal image IR will vary with the quality of the total optical system through which the projected reference image I travels, including the optical elements of the image projection system 102 and the ocular imaging system S of eye E. As can be understood with reference to FIGS. 4-5C, the object 104 may assume a variety of configurations such as reflective or transparent planar bodies, the object often defining a reference image as a grid, a set of sinusoidal wave gratings, an array of contrast bars of varying size, a Siemen's star, or the like.

Figure 3B:
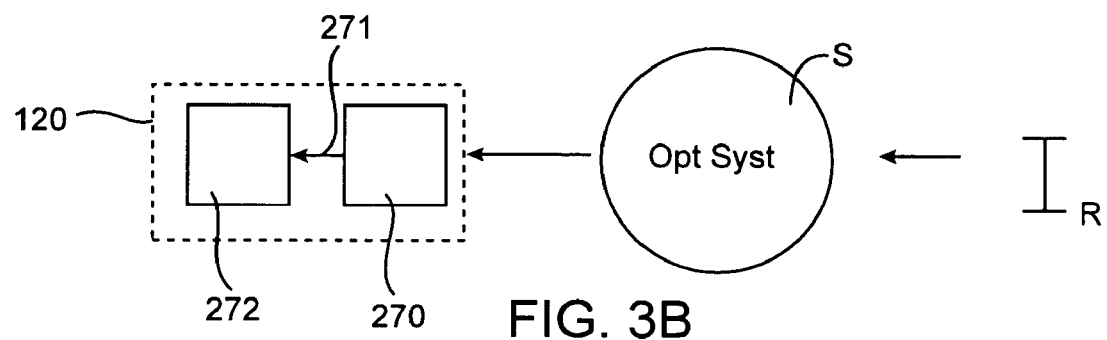

As can be understood with reference to FIGS. 2 and 3B, the retinal image IR projected in the interior of the eye E is imaged by a retinal image analyzer 120 (optionally via another beam splitter 112) to define an analysis image IE (see FIG. 5B). Based on the evaluation image IE imaged from the retina, the image analyzer 120 can be used to determine the current status of the ocular systems.

Image analyzer 120 will often comprise an image capture device 270 such as a charge-couple device (CCD), which converts the evaluation image into digital image signals 271 so that the image information can be analyzed by an image processor 272. Image Processor 272 will typically comprise hardware, software, and/or firmware arranged to calculate an optical characteristic of the evaluation image IE in response to image signals 271. Image Processor 272 will often determine optical quality, optionally by measuring the smallest features or spatial frequencies which are accurately reproduced in the evaluation image IE. More complex analysis may also be provided. The image processor 272 may be described as being an optical transfer function calculation device, a modulation transfer function calculation device, or the like, depending on which quality measurement is used within the system.

Advantageously, the image analyzer 120 can provide real time and/or intermittent information about a vision correction procedure before, during, and/or after the laser surgery procedure, as the projection optics 102 and imaging optics 105 do not interfere with the operation and/or alignment of the laser 12. Optionally, feedback during a resculpting may be provided while ablation is taking place and/or between pulses or partial treatments (to improve signal-to-noise performance) as object 104 and feedback assembly 120 are both upstream of the beam splitter 100 within the optical train 130. Preferably, the beam splitter 100 is an ultraviolet beam splitter which does not interfere with visible light rays and/or infrared energy coming from object 104.

Although the retinal image analyzer 120 may operate on a variety of different principles, a preferred embodiment of the analyzer 120 uses an optical transfer function (OTF) to determine a quality of the imaging provided by the corneal optical system S. The optical transfer function is a general measure of how well an optical system can transmit or transfer an image.

In general terms, the light or energy from an object 104 passing through an optical system 140 as indicated by arrows 142 will be produce an image of the object. In a perfect optical system, an image of object 104 would be perfectly recreated after passing through the optical system 140. In real systems, however, aberrations in any of the components of optical system 140 cause distortion and diffraction that create a less than perfect image transfer. Analysis of the image (IR in our example) that is actually created by the optical system allows the quality of the optical system to be accurately measured. More specifically, by analyzing the retinal image IR, and particularly by comparing the retinal image IR to the reference image I, an optical transfer function of optical system 140 can be determined. As the optical properties of the optical train 130 of system 10 can be readily determined, this allows the optical quality of the ocular optical system to be calculated. While the optical transfer function is a particularly advantageous measurement of optical imaging quality, it should be understood that a wide variety of known alternative optical quality measurements might be calculated.

Optical feedback system 30 will typically not derive the optical transfer function (or any other alternative measurement of imaging quality) directly from the retinal image IR, but will instead measure the imaging quality of the ocular optical system by imaging the retinal image IR from the retina onto the image capture device 270, so that the image again passes through the ocular optics. Thus, the final evaluation image IE will be defined by a reference image I which has passed twice through cornea C and the other components of the ocular optical system.

Figure 4:
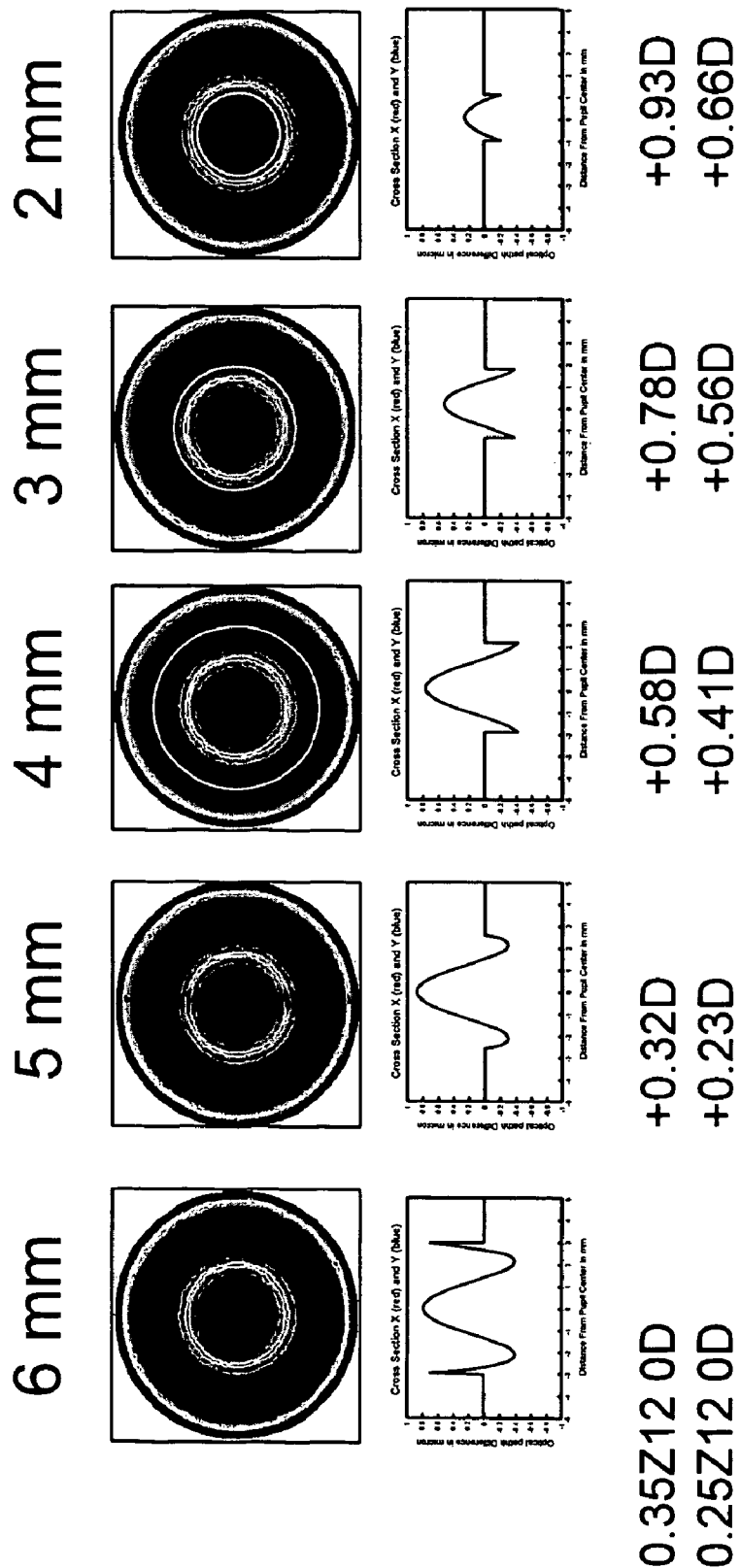
FIG. 4 is a chart showing various refractions by Zernike decomposition.

Theoretically, the optical transfer function may be defined by: OTF=MTF×PTF. In other words, the optical transfer function is the product of a modulation transfer function (MTF) and a phase transfer function (PTF). The modulation transfer function describes the way that the optical system 140 transfers contrast or modulation from object 104 to image I, as a function of spatial frequency. It relates to amplitude and intensity. The object 104 typically defines an image I as a pattern of lines with spatial separations or frequencies which vary according to a known pattern. A variety of these patterns are shown in FIGS. 4, 5A, and 5C. Typically, square wave gratings are used since they are easier to make, although their use often involves more data processing to extract the sinusoidal components used in MTF. Optionally, the modulation transfer function alone may be used as a measurement of imaging quality.

In a perfect optical system, the modulation transfer function approaches one. The modulation transfer function, also known as the sine wave response and contrast transfer function, measures the ability of an optical system to reproduce or transfer various levels of detail from the object to the image, as shown by the degree of contrast (modulation) in the image. As one might expect, the finer the detail, the higher the contrast required to resolve it.

The second component of the optical transfer function is the phase transfer function (PTF). It relates to image distortion or phase, and may optionally be disregarded when calculating the optical quality of the optical system.

Advantageously, the optical transfer function and/or modulation transfer function of an optical system can directly be determined by imaging gratings through the optical system. The contrasts in the object or reference image I and the evaluation image IE are measured, and their ratio can define the modulation transfer function for the spatial frequency of the grating. Similarly, imaging quality may be measured by determining the resolution power of the optical system, such as by measuring the smallest detail that can be detected or discriminated in an image.

Still further optical imaging quality measurement calculation methods might be used, such as determining the contrast threshold function, and the like. These and other standard optical imaging quality measurements are known and are described, for example, by George Smith et al. in "*The Eye and Visual Optical Instruments,*" Cambridge University Press (1997) pp. 662-691, by F. W. Campbell et al. in "*Optical Quality of the Human Eye,*" J.Physiol., 186 (October 1966), pp. 558-578; "*Photonics Dictionary,*" pp. D-22, 92, 102, and 123 (1997); and by William D. Stanley et al. in "*Digital Signal Processing,*" 2dEd., (1984) pp.120-124; the full disclosures of which are incorporated herein by reference.

Typically, one or more parameters of image quality are used to formulate a refractive correction plan from wavefront measurements. Some of the possible image quality parameters include the Strehl Ratio, root mean squared (RMS), the value of individual Zernike terms, full-width half-height (FWHH) of the point spread function (PSF), and modulation transfer function (MTF). For example, and with reference now to FIG. 4, based on a minimized wavefront RMS, spherical and cylindrical corrections can be determined by the second-order Zernike terms. This approach is effective when an eye has few high-order aberrations. When an eye has a significant quantity of high-order aberrations, however, minimizing the wavefront RMS does not necessarily lead to best image quality. Additionally, when the eye has a significant amount of spherical aberration, the refractive correction determined by the second-order Zernike terms will vary significantly depending on the pupil size of wavefront data. For an eye with Zernike spherical aberration equal to 0.35 um for a 6 mm pupil, the difference in spherical correction determined by Zernike decomposition can be as large as 0.93 D for pupil diameters varying from 2 mm to 6 mm. This large variation in refractive corrections, depending on the pupil size, contradicts the results seen in clinical refraction and can make the use of wavefront measurements for determining refractive corrections difficult.

Figure 5:
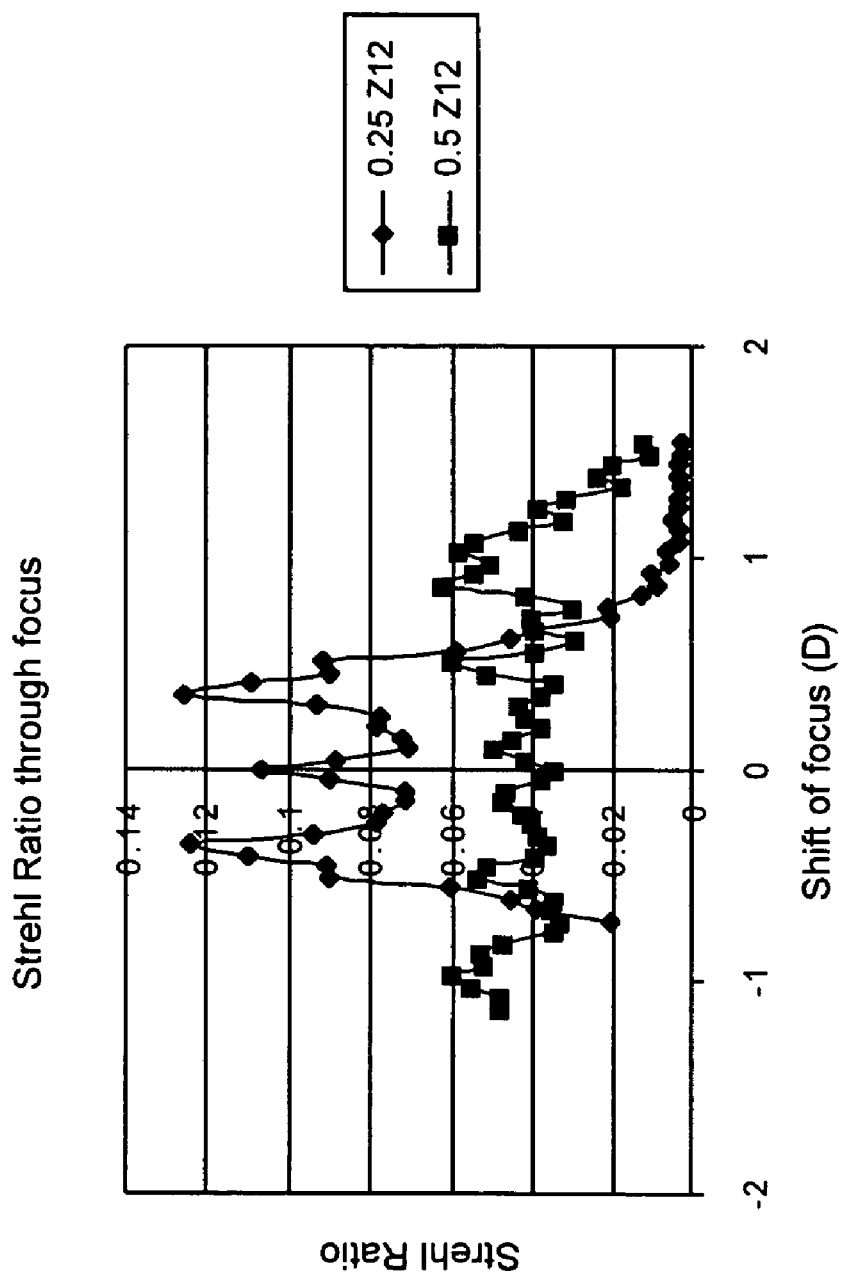
FIG. 5 is a graph showing a measured Strehl ratio.

Referring now to FIG. 5, another commonly used parameter is the Strehl Ratio, with a maximized Strehl Ratio often being used to determine refractive correction. The Strehl Ratio, however, covers the total MTF volume up to a cutoff spatial frequency that is typically around 180 cycles/degree for a 6 mm pupil. Spatial frequencies higher than about 60 cycles/degree have little or no bearing on actual vision, because the Nyquist frequency limit dictates that the average retinal receptor is capable of only about 57 cycles/degree. Thus, the Strehl Ratio may include information which is not helpful for refractive correction determination and multiple peaks in a Strehl Ratio curve may make determining an optimal refractive correction difficult.

Figure 6:
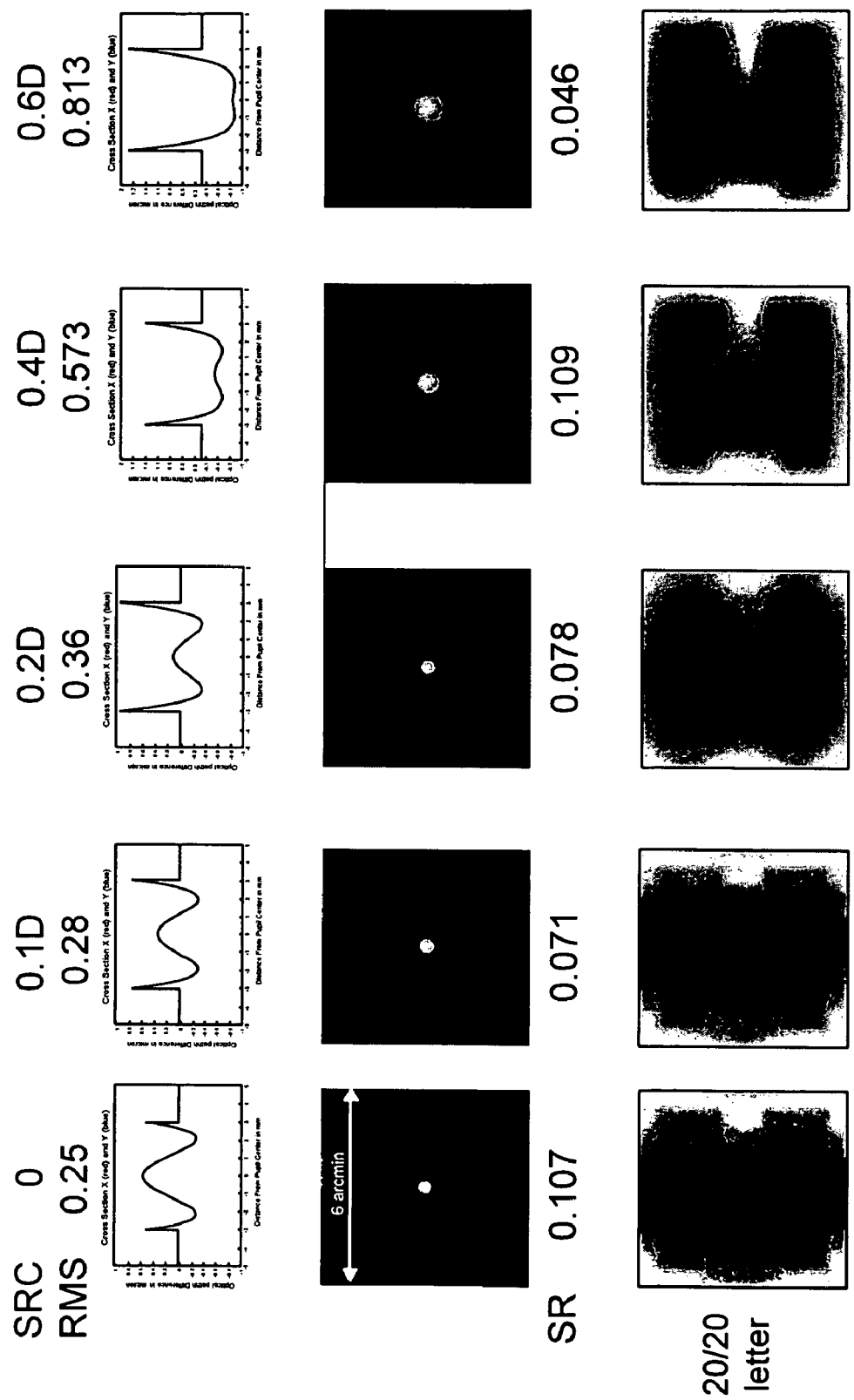
FIG. 6 is a chart showing image quality and Strehl Ratios at multiple refractive corrections.

FIG. 6 similarly demonstrates that choosing a refractive correction based on a maximized Strehl Ratio may not provide an optimal vision correction. As can be seen from the line labeled SR (for Strehl Ratio), the Strehl Ratio for a correction of 0D (0.107) and for a correction of 0.4 D (0.109) are almost identical. Yet, as seen from the 20/20 letter E, on the lowest line, actual vision quality is radically different between the two refractive corrections.

Figure 7:
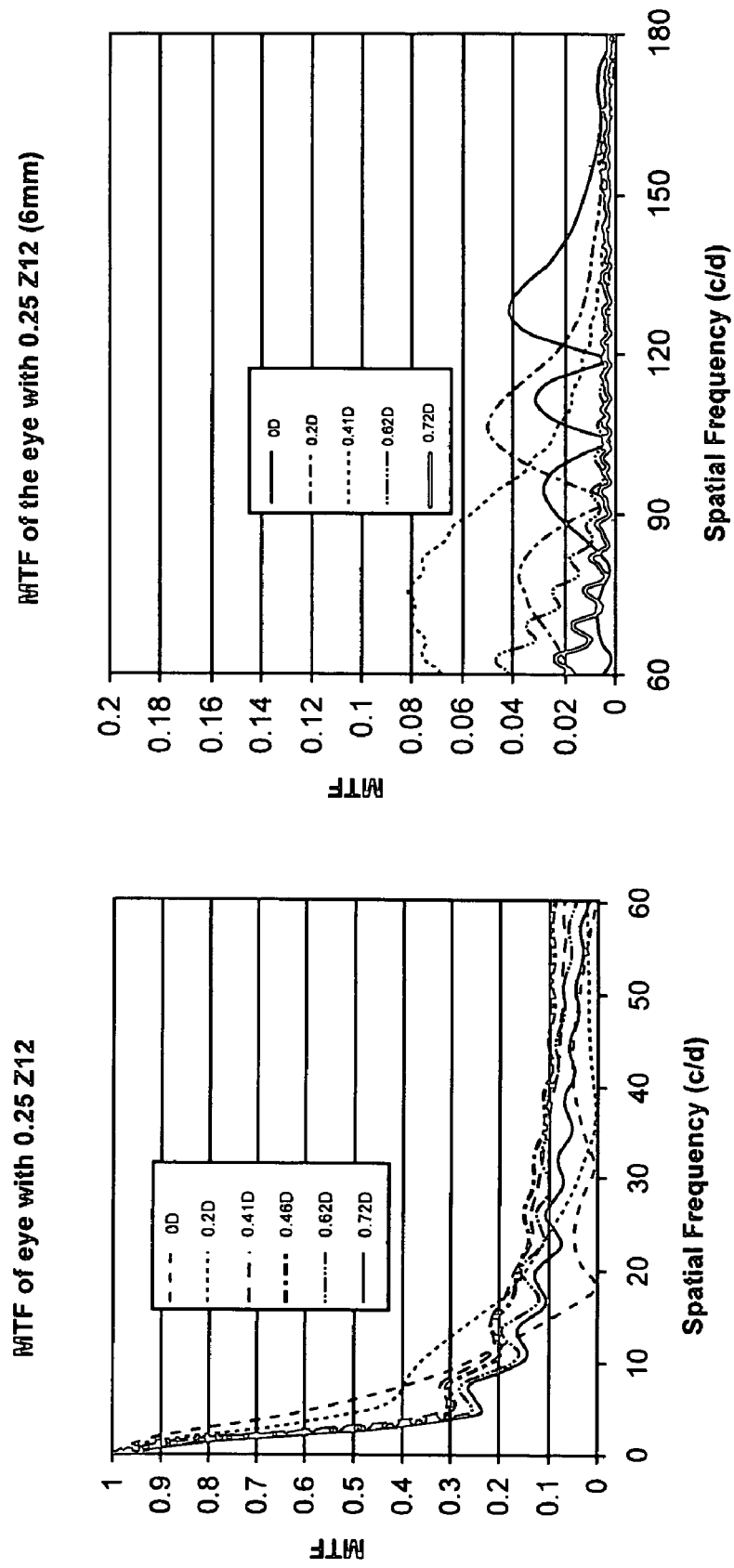
FIG. 7 is a graph showing multiple MTFs calculated over a range of spatial frequencies, according to one embodiment of the invention.
Figure 8:
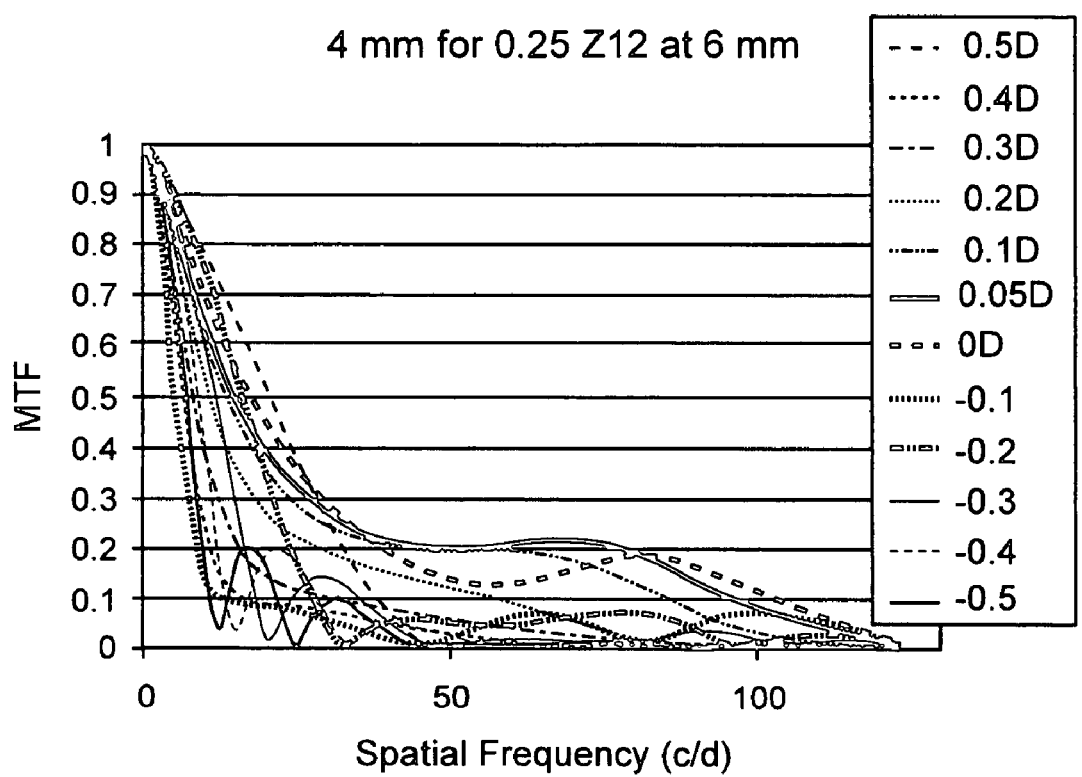
FIG. 8 is a graph showing multiple MTFs for a 4 mm pupil for 0.25 Z12 at 6 mm.

Referring now to FIG. 7, MTF through focus for 0.25 Z12 Zernicke polynomial is shown, with the various MTF curve corresponding to various, mathematically derived refractive corrections (shown in white boxes). The highest Strehl Ratio corresponds to the largest MTF volume (area under MTF curve) over a wide range of spatial frequencies, typically from 0 cycles/degree to about 180 cycles/degree. On the left side of FIG. 7, the MTF curves are shown within the spatial frequency range of between 0 cycles/degree and 60 cycles/degree, while on the right side of FIG. 7 the MTF curves are shown within the spatial frequency range of between 60 cycles/degree and 180 cycles/degree. The conventional definition of a Strehl ratio relates to the MTF across the entire spectrum from 0 cycles/degree to 180 cycles/degree. One currently used method for determining refractive correction seeks the correction which results in the highest Strehl ratio. However, MTF of the eye at frequencies higher than 60 cycles/degree does not correlate with improved vision, because the human eye has a frequency limit (known as the Nyquist frequency limit) of about 57 cycles/degree. Essentially, retinal photoreceptors cannot process spatial frequencies above this limit.

Therefore, due to the natural limits of retinal photoreceptors, it has been found that limiting imaging quality measurement calculations to specific frequency ranges or to a specific frequency may provide for improved determination of refractive corrections. Any of a number of suitable frequency ranges or specific frequencies may be used, with similar results. For example, in various embodiments, a range may comprise 60 cycles/degree and below, a smaller range within the range of 0 to 60 cycles/degree or a range having an upper frequency slightly over 60 cycles/degree. More specifically, some advantageous ranges may include, but are not limited to, about 0-60 cycles/degree, about 20-60 cycles/degree, about 0-80 cycles/degree and the like. In other embodiments, an image quality measurement may be measured for a specific frequency, such as 60 cycles/degree.

As mentioned above, MTF over selected frequency ranges or at a selected frequency comprises one of the imaging quality measurement calculations which may be used to determine refractive correction. When MTF volume over a frequency range is calculated, this may be referred to as a "modified Strehl ratio," with the word "modified" describing the fact that the range of spatial frequencies over which the MTF is calculated to derive the Strehl ratio is limited to a range that is narrower than 0-180 cycles/degree. Other imaging quality measurement calculations may similarly be limited to selected spatial frequencies or frequency ranges with advantageous effects, but in some embodiments MTF or modified Strehl ratio (which are sometimes synonymous) is used.

The multiple MTFs shown in FIG. 7 (shown as multiple lines on the graphs) correspond to multiple potential refractive corrections of an eye. It has been found that determining a highest of the MTFs at certain spatial frequencies and selecting the refractive correction that results in that highest MTF will result in an optimal refractive correction. Alternatively, MTF volumes may be measured as areas under the MTF curves. A refractive correction corresponding to the largest of the volumes over a limited range of frequencies may also provide an optimal refractive correction. In another embodiment, averages of MTFs may be used and the largest average MTF over a selected range of spatial frequencies may give an optimal refractive correction. Any of the above methods may be used with similar results. Alternatively or additionally, a modified Strehl ratio may be used, with the highest modified Strehl ratio corresponding to an optimal refractive correction.

For image quality measurement, the MTF of the eye at any of a number of different spatial frequencies may be examined. In some embodiments, for example, MTF may be calculated at 30 cycles/degree, which will typically be used as a base frequency for achieving 20/20 vision. In another embodiment, 37.5 cycles/degree may be used as a base frequency for 20/16 vision, 48 cycles/degree may be used as a base frequency for 20/12.5 vision, 60 cycles/degree may be used as a base frequency for 20/10 vision and/or the like. Similarly, many different spatial frequency ranges may be used in various embodiments. In one embodiment, for example, MTF between about 0 cycles/degree and about 60 cycles/degree may be calculated. In another embodiment, MTF between about 20 cycles/degree and about 60 cycles/degree may be calculated. In still another embodiment, MTF between about 0 cycles/degree and about 80 cycles/degree may be calculated. Thus, any suitable spatial frequency or spatial frequency range is contemplated. Generally, however, methods and systems of the invention involve limiting image quality measurement calculations to a selected frequency or range of frequencies, rather than using a conventional Strehl ratio, for example, which spans an all-inclusive range of frequencies.

Figure 9:
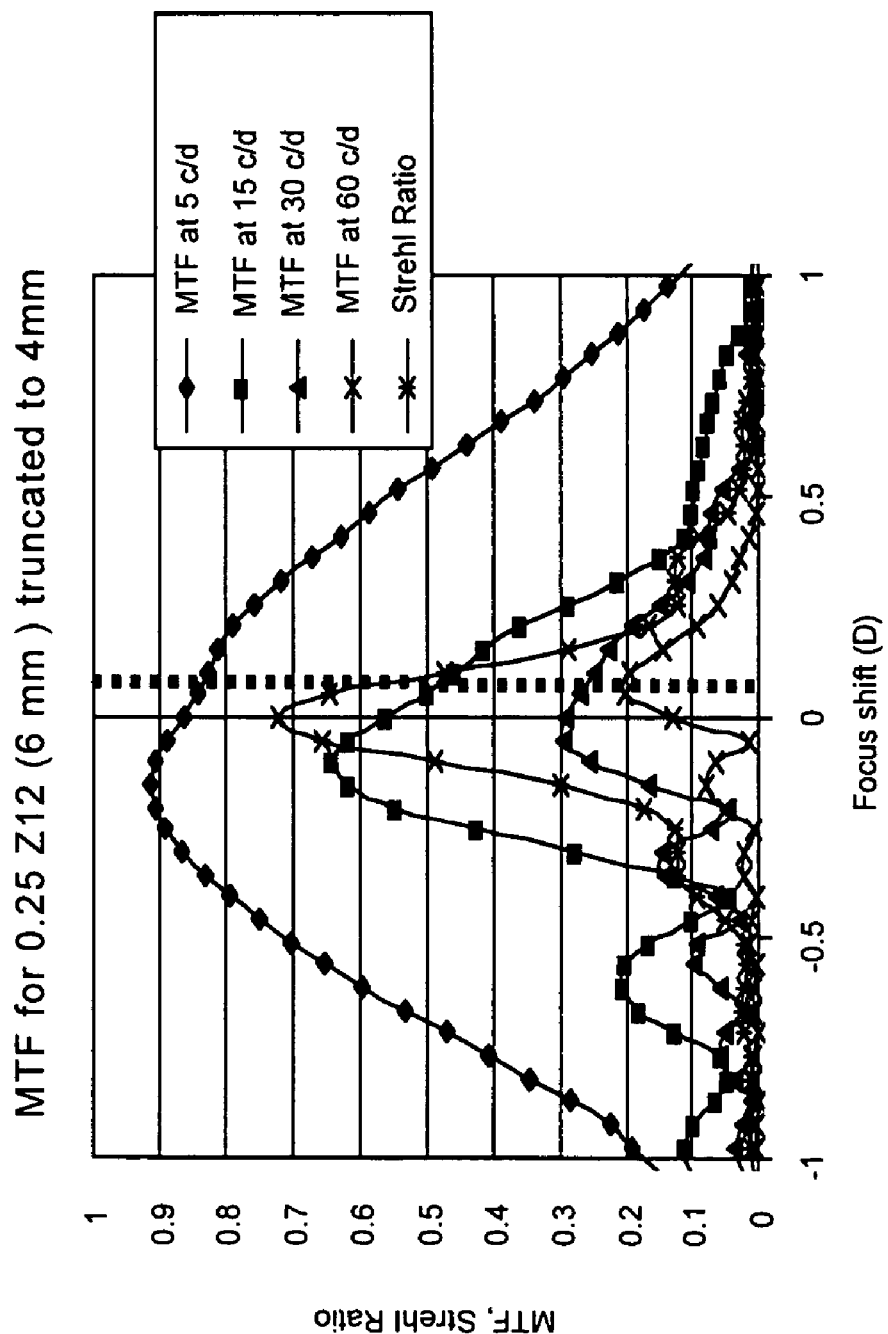
FIG. 9 is a graph showing multiple MTFs and an optimal refraction for pupils of different size, according to one embodiment of the invention.

With reference now to FIGS. 8-11, it has also been found that measurement of MTF within a selected frequency range or at a selected frequency provides for refractive corrections that enhance vision of both a 4 mm pupil and a 6 mm pupil and which apply for different amounts of spherical aberration. For example, as shown in FIG. 9, using MTFs with a through focus truncated to 4 mm for 0.25 Z12 at 6 mm, one can arrive at an optimal focus shift to enhance vision with both a 4 mm pupil and a 6 mm pupil. In the example in FIG. 9, this shift is 0.05D. FIG. 10 shows that using methods of the present invention provides for net shift foci for a 6 mm pupil (−0.29 in this example) and a 4 mm pupil (−0.28 in this example) which are nearly identical. FIG. 11 shows that basing refractive correction on a maximized MTF at 60 cycles/degree will result in similar visual acuity, when spherical aberration is within a range of between approximately −0.7 microns and about 0.7 microns.

Thus, in general terms, a method of the present invention for determining a refractive correction for an eye may comprise: measuring an optical error of the eye; calculating at least one image quality parameter for a selected spatial frequency or range of spatial frequencies, based on the measured optical error of the eye; and forming a plan for refractive correction of the optical error, based on the calculated image quality parameter. In some embodiments, measuring the optical error of the eye will include taking a wavefront measurement, but other measurements may be suitable in other embodiments. In many embodiments, one or more MTFs may be calculated as the image quality parameter over a range of frequencies or at one frequency, as described in detail above. And in some embodiments, forming a plan for refractive correction may involve planning a laser ablation procedure on an eye. Any suitable variations of such methods are contemplated.

Devices and systems for implementing the methods of the invention may take any suitable form. In some embodiments, devices will comprise one or more software modules for processing data, such as wavefront measurement data, to arrive at refractive corrections. Devices may also include hardware, such as a processor for processing data to arrive at refractive corrections. Systems for measuring and/or operating on a eye may include software and/or hardware to achieve the methods of the present invention. In one embodiment, a system includes both a sensor, for sensing an optical error of an eye, and a processor, for processing the sensed optical error into a refractive correction. A system may comprise, for example, any of the systems described above in detail for conducting a laser surgery procedure on an eye, any other suitable laser eye surgery systems, or any other suitable vision correction system. Any suitable device, system or combination for achieving the methods of the invention is contemplated.

A variety of refinements, adaptations, and modifications are possible within the scope of the present invention. Hence, the scope of the present invention is not limited to the specifics of the exemplary embodiment, but is instead limited solely by the appended claims.

What is claimed is:

1. A method for determining a refractive correction for an eye, the method comprising:
measuring a high-order optical error of the eye;
calculating at least one image quality parameter for a selected spatial frequency or range of spatial frequencies, based on the measured optical error of the eye, wherein the selected frequency is or range of frequencies are selected in response to capabilities of photoreceptors of the eye; and
forming a plan for refractive correction of the optical error, based on the calculated image quality parameter.

2. A method as in claim 1, wherein measuring the optical error comprises measuring at least one wavefront aberration with a wavefront of light passing through the optical components of the eye, using a wavefront sensor.

3. A method as in claim 2, wherein the wavefront aberration is measured with the pupil of the eye having a diameter of between about 4 mm and about 6 mm.

4. A method as in claim 1, wherein calculating at least one image quality parameter comprises calculating at least one modulation transfer function.

5. A method as in claim 4, wherein calculating at least one modulation transfer function comprises calculating a plurality of modulation transfer functions corresponding to a plurality of potential refractive corrections.

6. A method as in claim 5, wherein forming a plan for refractive correction comprises selecting one of the potential refractive corrections, wherein the selected refractive correction corresponds to a highest modulation transfer function of the plurality of modulation functions, at the selected spatial frequency.

7. A method for determining a refractive correction for an eye, the method comprising:
measuring an optical error of the eye;
calculating at least one image quality parameter for a selected spatial frequency or range of spatial frequencies, based on the measured optical error of the eye, wherein calculating at least one image quality parameter comprises calculating a plurality of modulation transfer functions corresponding to a plurality of potential refractive corrections; and
forming a plan for refractive correction of the optical error, based on the calculated image quality parameter, wherein forming a plan for refractive correction comprises selecting one of the potential refractive corrections, wherein the selected refractive correction corresponds to a largest total volume modulation transfer function of the plurality of modulation functions, over the selected range of spatial frequencies.

8. A method for determining a refractive correction for an eye, the method comprising:
measuring an optical error of the eye;
calculating at least one image quality parameter for a selected spatial frequency or range of spatial frequencies, based on the measured optical error of the eye, including calculating a plurality of modulation transfer functions corresponding to a plurality of potential refractive corrections; and forming a plan for refractive correction of the optical error, based on the calculated image quality parameter by selecting one of the potential refractive corrections, wherein the selected refractive correction corresponds to a highest average modulation transfer function of the plurality of modulation functions, over the selected range of spatial frequencies.

9. A method as in claim 1, wherein calculating at least one image quality parameter comprises calculating at least one modified Strehl ratio.

10. A method for determining a refractive correction for an eye, the method comprising:

measuring an optical error of the eye;

calculating at least one image quality parameter for a selected spatial frequency or range of spatial frequencies, based on the measured optical error of the eye, including calculating at least one modified Strehl ratio; and forming a plan for refractive correction of the optical error, based on the calculated image quality parameter;

wherein calculating at least one modified Strehl ratio comprises calculating a plurality of modified Strehl ratios corresponding to a plurality of potential refractive corrections within the selected range of spatial frequencies comprising about 0 cycles/degree to about 60 cycles/degree.

11. A method as in claim 10, wherein forming a plan for refractive correction comprises selecting one of the potential refractive corrections, wherein the selected refractive correction corresponds to a highest modified Strehl ratio of the plurality of modified Strehl ratios.

12. A method as in claim 1, wherein the selected spatial frequency comprises about 30 cycles/degree.

13. A method as in claim 1, wherein the selected spatial frequency comprises about 37.5 cycles/degree.

14. A method as in claim 1, wherein the selected spatial frequency comprises about 48 cycles/degree.

15. A method as in claim 1, wherein the selected spatial frequency comprises about 60 cycles/degree.

16. A method as in claim 1, wherein the selected range of spatial frequencies comprises about 0 cycles/degree to about 60 cycles/degree.

17. A method as in claim 1, wherein the selected range of spatial frequencies comprises about 20 cycles/degree to about 60 cycles/degree.

18. A method as in claim 1, wherein the selected range of spatial frequencies comprises about 0 cycles/degree to about 80 cycles/degree.

19. A method as in claim 1, wherein forming a plan for refractive correction comprises calculating an ablation pattern for a corneal tissue of the eye, based at least partly on the calculated image quality parameter.

20. A method as in claim 19, further comprising ablating the corneal tissue of the eye according to the ablation pattern.

21. A system for determining a refractive correction for an eye, the system comprising:

a sensor for measuring a high-order optical error of the eye; and a processor for generating a refractive correction pattern based at least in part on an image quality parameter for a selected spatial frequency or range of spatial frequencies the spectral frequency or range of spatial frequencies corresponding to the capabilities of photoreceptors of the eye, the image quality parameter being based on the optical error.

22. A system as in claim 21, wherein the sensor comprises a wavefront sensor.

23. A system as in claim 21, wherein the image quality parameter comprises at least one modulation transfer function.

24. A system as in claim 21, wherein the image quality parameter comprises at least one modified Strehl ratio.

25. A system as in claim 24, wherein the modified Strehl ratio comprises a Strehl ratio limited to a range of spatial frequencies of between about 0 cycles/degree and about 60 cycles/degree.

26. A system as in claim 21, wherein the refractive correction pattern comprises an ablation pattern of laser energy for ablation of a corneal tissue of the eye so as to correct the measured optical error.

27. A system as in claim 26, the system further comprising a laser system for directing laser energy onto the corneal tissue of the eye to achieve the generated ablation pattern.

28. A system for correcting haul a high-order optical error of an eye, the system comprising:

a sensor for measuring the optical error of the eye;

a processor for generating an ablation pattern of laser energy for ablation of a corneal tissue of the eye so as to correct the measured optical error, the ablation pattern based at least in part on an image quality parameter for a selected spatial frequency or range of spatial frequencies, the spectral frequency or range of spatial frequencies being limited to less than 60 cycles/degree so as to correspond to the capabilities of photoreceptors of the eye, the image quality parameter being based on the optical error; and a laser system for directing laser energy onto the corneal tissue of the eye to achieve the generated ablation pattern.

29. A device for determining a high-order refractive correction for an eye, the device comprising a software module for processing at least one measurement of the eye to provide the refractive correction of the eye, the software module comprising computer-readable media embodying instructions for determining an image quality parameter for a spatial frequency or range of spatial frequency corresponding to capabilities of photoreceptors of the eye, and for outputting the correction.

30. A device as in claim 29, wherein the at least one measurement comprises at least one wavefront measurement.

31. A device as in claim 29, wherein the software module calculates at least one modulation transfer function, based on the at least one measurement.

* * * * *